United States Patent [19]
Moest

[11] Patent Number: 5,320,852
[45] Date of Patent: Jun. 14, 1994

[54] ANTACID MICROTABLETS

[75] Inventor: Thomas Moest, Moorrege, Fed. Rep. of Germany

[73] Assignee: Nordmark Arzneimittel GmbH, Uetersen, Fed. Rep. of Germany

[21] Appl. No.: 987,559

[22] Filed: Dec. 8, 1992

Related U.S. Application Data

[63] Continuation of Ser. No. 602,788, Oct. 24, 1990, abandoned.

[30] Foreign Application Priority Data

Nov. 10, 1989 [DE] Fed. Rep. of Germany ....... 3937455

[51] Int. Cl.$^5$ .................. A61K 9/20; A61K 33/08; A61K 33/10; A61K 33/12
[52] U.S. Cl. ................... 424/464; 424/465; 424/470; 424/682; 424/683; 424/690; 424/692; 514/819; 514/960
[58] Field of Search ............... 424/464, 465, 439, 466, 424/470, 682, 683, 690, 692; 514/819

[56] References Cited

U.S. PATENT DOCUMENTS

| 3,501,571 | 3/1970 | Yen | 424/470 |
| 4,004,036 | 1/1977 | Schmitt | 426/658 |
| 4,666,703 | 5/1987 | Kopf | 424/470 |
| 4,704,269 | 11/1987 | Korab | 424/466 |
| 4,797,287 | 1/1989 | Pich et al. | 424/464 |
| 4,828,843 | 5/1989 | Pich et al. | 424/464 |

OTHER PUBLICATIONS

Facts and Comparisons, J. B. Lippincott Co. Mar. 1984, p. 248 F, Olin, B. R. et al.
Facts and Comparisons, Olin, B. R. et al., Antidotes, p. 713 C, Feb. 1988, J. B. Lippincott Co.

Primary Examiner—Thurman K. Page
Assistant Examiner—james M. Spear
Attorney, Agent, or Firm—Oblon, Spivak, McClelland, Maier & Neustadt

[57] ABSTRACT

A biconvex tablet whose height and diameter are approximately equal and are from 1.5 to 4 mm and which, besides conventional pharmaceutical auxiliaries, contains an antacid as active substance is described.

3 Claims, No Drawings

ANTACID MICROTABLETS

This application is a continuation of application Ser. No. 07/602,788, filed on Oct. 24, 1990, now abandoned.

The present invention relates to small antacid tablets, 50 to 1000 of which are swallowed with liquid per dose. This avoids the unpleasantness associated with taking conventional antacid forms.

Drugs which have to be taken in high doses and are unpleasant to take in that they cause deposits on and between the teeth and in the mouth meet with resistance from patients (low patient compliance).

Antacids are examples of this, it often being necessary to take from 1 to 3 g, and are commercially available in the form of chewable tablets or gels. Chewable tablets cause long-lasting deposits on the teeth when chewed, and these persist in an unpleasant manner for a long period because of the sandy texture of the insoluble active substance. Gels involve tiresome preparation by tearing open and kneading a sachet to expel the gel, possibly with stirring in water and/or application to the mouth. Once again, the insoluble substances are deposited between the teeth and in the mouth.

It is an object of the present invention to develop a form for antacids which avoids the unpleasantness of taking them.

We have found that this object is achieved by biconvex tablets whose height and diameter are approximately the same and are from 1.5 to 4 mm and which, besides conventional pharmaceutical auxiliaries, contain an antacid as active substance. These small tablets are easy to swallow and do not remain adherent in the mouth.

Antacids are substances which counter hyperacidity of gastric juice (heartburn). Examples of suitable compounds are magnesium hydroxide, oxide, carbonate and silicate, aluminum hydroxide and phosphate, and magnesium aluminum silicates. The former use of sodium bicarbonate has been abandoned. Antacids are generally employed in amounts of from 60 to 95% by weight, preferably 65 to 90% by weight, based on the tablet (without coating).

The tablets are produced with conventional pharmaceutical auxiliaries in proportions of from 2 to 20% with a diameter of from 1.5 to 4 mm in biconvex form, with the height being approximately equal to the diameter (±max. 25%, preferably max. 10%). It is not necessary for all surfaces to be convex, on the contrary they can be manufactured with a narrow flat rim.

Examples of conventional pharmaceutical auxiliaries are binders such as lactose, starch, gelatin, microcrystalline cellulose or polyvinylpyrrolidone (PVP), disintegrants such as crosslinked PVP, corn starch, starch glycolate or alginic acid, lubricants such as magnesium stearate or talc, and flow regulators such as highly disperse silica.

In order to avoid an unpleasant taste and to improve the ease of swallowing, the tablets can be provided by conventional processes with coatings of water-soluble polymers or sugar. The polymers which are preferably employed are water-soluble cellulose derivatives such as methylcellulose or hydroxypropylmethylcellulose, and PVP.

From 50 to 500 such tablets of appropriate size and the desired dosage can be used as granules with conventional measuring appliances such as measuring spoons or dose dispensers, or else packed in single-dose sachets. No residue is left in the mouth after intake with a reasonable amount of liquid.

Inclusion of disintegrants in the tablet formulation can be used to ensure that each tablet rapidly disintegrates in the stomach so that, in conjunction with the large surface area and the distribution of the tablets in the volume of the stomach, rapid availability of the active substance is ensured.

The small tablets can be produced, for example, as described in U.S. Pat. Nos. 4,797,287 and 4,828,843.

EXAMPLE 1

| Composition | Dose unit | Batch |
| --- | --- | --- |
| 1. Aluminum hydroxide (dried gel) | 600 mg | 1.20 kg |
| 2. Magnesium hydroxide (powder) | 210 mg | 0.42 kg |
| 3. Lactose | 50 mg | 0.10 kg |
| 4. Polyvinylpyrrolidone | 35 mg | 0.07 kg |
| 5. Crosslinked polyvinylpyrrolidone | 40 mg | 0.08 kg |
| 6. Highly disperse silica | 5 mg | 0.01 kg |
| 7. Magnesium stearate | 20 mg | 0.04 kg |

Production of 2000 dose units

Ingredients 1. to 3. were mixed in a high-performance laboratory mixer (Stephan UMC 12) and granulated with an 8% aqueous solution of 4. The granules were passed through a 1.0 mm screen and then dried in a circulating air oven at 60° to 70° C. The dry granules were passed through a 0.63 mm screen and then initially mixed with 5. and 6. and finally mixed with added 7.

The composition ready for tableting was compressed in an eccentric press with 2.5 mm concave dies to give microtablets which were 2.5 mm high and weighed 2.0 mg each.

80 of these microtablets comprise a dose unit. The disintegration time (Ph. Eur. method) of the microtablets is 9 min, and they can easily be swallowed with a glass of water without unpleasant sensations.

EXAMPLE 2

| Composition | Dose unit | Batch |
| --- | --- | --- |
| 1. Aluminum hydroxide (dried gel) | 500 mg | 1.00 kg |
| 2. Calcium carbonate (heavy, powder) | 100 mg | 0.20 kg |
| 3. Magnesium hydroxide (powder) | 200 mg | 0.40 kg |
| 4. Polyvinylpyrrolidone | 30 mg | 0.06 kg |
| 5. Lactose, directly tabletable | 130 mg | 0.26 kg |
| 6. Microcrystalline cellulose | 100 mg | 0.20 kg |
| 7. Corn starch | 100 mg | 0.20 kg |
| 8. Highly dispersed silica | 10 mg | 0.02 kg |
| 9. Magnesium stearate | 30 mg | 0.06 kg |
| 10. Hydroxypropylmethylcellulose | 20 mg | 0.04 kg |

Production of 2000 dose units

Ingredients 1. to 3. were mixed in a high-performance laboratory mixer (Stephan UMC 12) and granulated with an 8% aqueous solution of 4. The granules were passed through a 1.2 mm screen and then dried in an oven at 60° C. The dry granules were passed through a 0.8 mm screen and then initially mixed with 5. to 8. and finally mixed with added 9.

The composition ready for tableting was compressed in an eccentric press with 3 mm concave dies to give microtablets which were 3 mm high and weighed 20 mg each.

A 5% aqueous solution of 10. was sprayed onto the microtablets in a fluidized bed (Glatt WSG 5) with the inlet air at 50° C.

60 of these microtablets comprise a dose unit. The disintegration time (Ph. Eur. method) of the microtablets is 8 min. They can easily be swallowed with a glass of water without unpleasant sensations.

I claim:

1. A biconvex tablet whose height and diameter are approximately equal and are from 1.54–4 mm and which, besides conventional pharmaceutical auxiliaries, contains as an active agent in amount of 60–95 percent by weight an antacid, which antacid is selected from the group consisting of magnesium hydroxide, magnesium oxide, magnesium carbonate, magnesium silicate, aluminum hydroxide, aluminum phosphate, magnesium aluminum silicate, and mixtures thereof.

2. A tablet as claimed in claim 1 with a diameter of from 2 to 3 mm.

3. The biconvex tablet of claim 1, wherein said antacid is at least one member selected from the group consisting of magnesium hydroxide, magnesium oxide, magnesium carbonate, magnesium silicate, aluminum hydroxide, aluminum phosphate, and magnesium aluminum silicate.

* * * * *